United States Patent
Manjeshwar et al.

(10) Patent No.: US 7,680,240 B2
(45) Date of Patent: Mar. 16, 2010

(54) ITERATIVE RECONSTRUCTION OF TOMOGRAPHIC IMAGE DATA METHOD AND SYSTEM

(75) Inventors: Ravindra Mohan Manjeshwar, Glenville, NY (US); Floribertus Philippus Martinus Heukensfeldt Jansen, Ballston Lake, NY (US); James William Hugg, Glenville, NY (US); Charles William Stearns, New Berlin, WI (US)

(73) Assignee: General Electric Company, Niskayuna, NY (US)

(*) Notice: Subject to any disclaimer, the term of this patent is extended or adjusted under 35 U.S.C. 154(b) by 266 days.

(21) Appl. No.: 11/731,612

(22) Filed: Mar. 30, 2007

(65) Prior Publication Data

US 2008/0240335 A1  Oct. 2, 2008

(51) Int. Cl.
 *A61B 6/00* (2006.01)
(52) U.S. Cl. .......................................... 378/4
(58) Field of Classification Search ............ 378/4, 378/8
 See application file for complete search history.

(56) References Cited

U.S. PATENT DOCUMENTS

| | | | | |
|---|---|---|---|---|
| 4,689,670 A | * | 8/1987 | Okazaki | 378/98.5 |
| 4,837,686 A | * | 6/1989 | Sones et al. | 378/18 |
| 5,053,958 A | * | 10/1991 | Tam | 378/4 |
| 5,400,377 A | * | 3/1995 | Hu et al. | 378/8 |
| 5,504,334 A | | 4/1996 | Jansen | |
| 5,561,695 A | * | 10/1996 | Hu | 378/8 |
| 5,602,891 A | * | 2/1997 | Pearlman | 378/62 |
| 5,625,190 A | * | 4/1997 | Crandall | 250/363.03 |
| 5,689,116 A | | 11/1997 | Heukensfeldt | |
| 5,802,133 A | * | 9/1998 | Kawai et al. | 378/4 |
| 6,226,350 B1 | * | 5/2001 | Hsieh | 378/98 |
| 6,442,235 B2 | * | 8/2002 | Koppe et al. | 378/62 |
| 6,445,761 B1 | * | 9/2002 | Miyazaki et al. | 378/8 |
| 6,522,712 B1 | * | 2/2003 | Yavuz et al. | 378/4 |
| 6,574,300 B1 | * | 6/2003 | Florent et al. | 378/19 |
| 6,654,440 B1 | * | 11/2003 | Hsieh | 378/4 |
| 6,768,782 B1 | * | 7/2004 | Hsieh et al. | 378/8 |
| 6,845,142 B2 | * | 1/2005 | Ohishi | 378/8 |
| 6,850,587 B1 | * | 2/2005 | Karimi et al. | 378/15 |

(Continued)

OTHER PUBLICATIONS

Ogawa et al., A Reconstruction Algorithm from Truncated Projections, IEEE Transactions on Medical Imaging, vol. MI-3, No. 1, Mar. 1984, pp. 34-40.*

(Continued)

*Primary Examiner*—Edward J Glick
*Assistant Examiner*—Alexander H Taningco
(74) *Attorney, Agent, or Firm*—Scott J. Asmus

(57) ABSTRACT

Methods for performing image reconstruction that include deriving background projection data for an area outside a targeted field of view of a tomographic image, and reconstructing the tomographic image of the targeted field of view, wherein the background projection data is used in the reconstruction. Methods for selecting a reconstruction methodology that include determining a number of pixels in a reconstructed image for a first reconstruction methodology, determining a number of pixels in a reconstructed image for a second reconstruction methodology, comparing the number of pixels for the first reconstruction methodology and the number of pixels for the second reconstruction methodology, and selecting the reconstruction methodology for image reconstruction based on the comparison of the number of pixels. Imaging systems implementing these methods are also provided.

29 Claims, 9 Drawing Sheets

U.S. PATENT DOCUMENTS

| | | |
|---|---|---|
| 7,006,677 B2 | 2/2006 | Manjeshwar |
| 7,038,212 B2 | 5/2006 | Wollenweber |
| 7,057,178 B1 | 6/2006 | Manjeshwar |
| 7,129,495 B2 | 10/2006 | Williams |
| 7,129,496 B2 | 10/2006 | Stearns |
| 7,173,248 B2 | 2/2007 | Ross |
| 2003/0081715 A1* | 5/2003 | Tam .............................. 378/4 |
| 2004/0066911 A1* | 4/2004 | Hsieh et al. .................. 378/901 |
| 2004/0225214 A1 | 11/2004 | Trotter |
| 2006/0097175 A1 | 5/2006 | Ganin |
| 2006/0138315 A1 | 6/2006 | Williams |
| 2006/0145082 A1 | 7/2006 | Stearns |
| 2006/0151705 A1 | 7/2006 | Manjeshwar |
| 2006/0261275 A1 | 11/2006 | Stearns |
| 2006/0262894 A1* | 11/2006 | Bernhardt et al. .............. 378/4 |

OTHER PUBLICATIONS

Wagner, Reconstructions From Restricted Region Scan Data—New Means to Reduce the Patient Dose, IEEE Transactions on Nuclear Science, vol. NS-26, No. 2, Apr. 1979, pp. 2866-2869.*

Nalcioglu et al., Limited Field of View Reconstruction in Computerized Tomography, IEEE Transactions on Nuclear Science, vol. NS-26, No. 1, Feb. 1979, pp. 1-6.*

* cited by examiner

ITERATIVE RECONSTRUCTION OF TOMOGRAPHIC IMAGE DATA METHOD AND SYSTEM

BACKGROUND

The invention relates generally to non-invasive imaging. More particularly, the invention relates to methods and systems for targeted iterative reconstruction for use in non-invasive imaging.

In the fields of medical imaging and security screening, non-invasive imaging techniques have gained importance due to benefits that include unobtrusiveness, ease, and speed. In medical and research contexts, these imaging systems are used to image organs or tissues beneath the surface of the skin. A number of non-invasive imaging modalities exist today. A particular modality may be selected based upon the organ or tissue to be imaged, upon the spatial and/or temporal resolution desired, or upon whether structural or functional characteristics are of interest. Certain of these non-invasive imaging modalities collect tomographic data that includes sets of line integrals from multiple directions. Examples of these imaging modalities include positron emission tomography (PET) imaging, single photon emission computed tomography (SPECT) imaging, x-ray computed tomography (CT) imaging, magnetic resonance imaging (MRI) using projection reconstruction, and x-ray tomosynthesis.

Certain applications of these imaging modalities require high-resolution images of a targeted field of view (FOV) that is less than the scan FOV for the imaging system. For example, in cardiac imaging, a high-resolution image of a small sub-region of the patient's anatomy may be desired. In emission tomography, e.g., PET or SPECT, the measured projection data contains activity from outside this targeted FOV. While reconstruction of this targeted FOV is generally straightforward for analytical reconstruction algorithms (such as filtered back projection), iterative reconstruction techniques typically require that the targeted FOV include the entire region of support of the image. This is because iterative reconstruction techniques attempt to match the estimated projection data (derived from forward projection of an estimated image) to the measured projection data. If the estimated projection data does not support the signal from outside the targeted FOV, the estimated projection data cannot correctly match the measured projection data.

In general, the signal from outside the targeted FOV should be accounted for in the image reconstruction. If the signal from outside the targeted FOV is not accounted for, the entire signal from outside the targeted FOV will be assigned to the periphery of the targeted FOV. However, this approach may result in a visible artifact at the periphery of the reconstructed image and quantitatively inaccurate regions throughout the reconstructed image. In other cases, when a targeted FOV less than the scan FOV is requested, the full scan FOV may be reconstructed at high resolution. Subsequently, the image for desired targeted FOV may be extracted from this image for the full scan FOV. This approach, however, reconstructs an image for a full pixel grid even though only a partial pixel grid for the targeted FOV was requested. As the computational time and image storage requirements grow significantly based on the number of pixels in the reconstruction, this approach may be computationally extensive.

BRIEF DESCRIPTION

In accordance with an exemplary embodiment of the present technique, a method for performing image reconstruction is provided. The method includes deriving background projection data for an area outside a targeted field of view of a tomographic image. The method further includes reconstructing the tomographic image of the targeted field of view, wherein the background projection data is used in the reconstruction of the tomographic image.

In accordance with another exemplary embodiment of the present technique, a method of selecting a reconstruction methodology. The method includes determining a number of pixels in a reconstructed image for a first reconstruction methodology, and determining a number of pixels in a reconstructed image for a second reconstruction methodology. The method further includes comparing the number of pixels for the first reconstruction methodology and the number of pixels for the second reconstruction methodology. The method further includes selecting the reconstruction methodology for image reconstruction based on the comparison of the number of pixels.

In accordance with another exemplary embodiment of the present technique, an imaging system is provided. The imaging system includes image reconstruction and processing circuitry configured to derive background projection data for an area outside a targeted field of view of a tomographic image, and to reconstruct the tomographic image of the targeted field of view, wherein the background projection data is used in the reconstruction.

In accordance with another exemplary embodiment of the present technique another imaging system is provided. The imaging system includes image reconstruction and processing circuitry configured to determine a number of pixels in a reconstructed image for a first reconstruction methodology, to determine a number of pixels in a reconstructed image for a second reconstruction methodology, to compare the number of pixels for the first reconstruction methodology and the number of pixels for the second reconstruction methodology, and to select the reconstruction methodology for image reconstruction based on the comparison of the number of pixels.

In accordance with another exemplary embodiment of the present technique a computer program, stored on a computer readable medium, for performing image reconstruction is provided. The program is constructed and arranged to derive background projection data for an area outside a targeted field of view of a tomographic image. The program is further constructed to reconstruct the tomographic image of the targeted field of view, wherein the background projection data is used in the reconstruction.

In accordance with yet another exemplary embodiment of the present technique, a computer program, stored on a computer readable medium, for selecting a reconstruction methodology is provided. The computer program is constructed and arranged to determine a number of pixels in a reconstructed image for a first reconstruction methodology and to determine a number of pixels in a reconstructed image for a second reconstruction methodology. The program is further constructed and arranged to compare the number of pixels for the first reconstruction methodology and the number of pixels for the second reconstruction methodology. The program is further constructed and arranged to select the reconstruction methodology for image reconstruction based on the comparison of the number of pixels.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
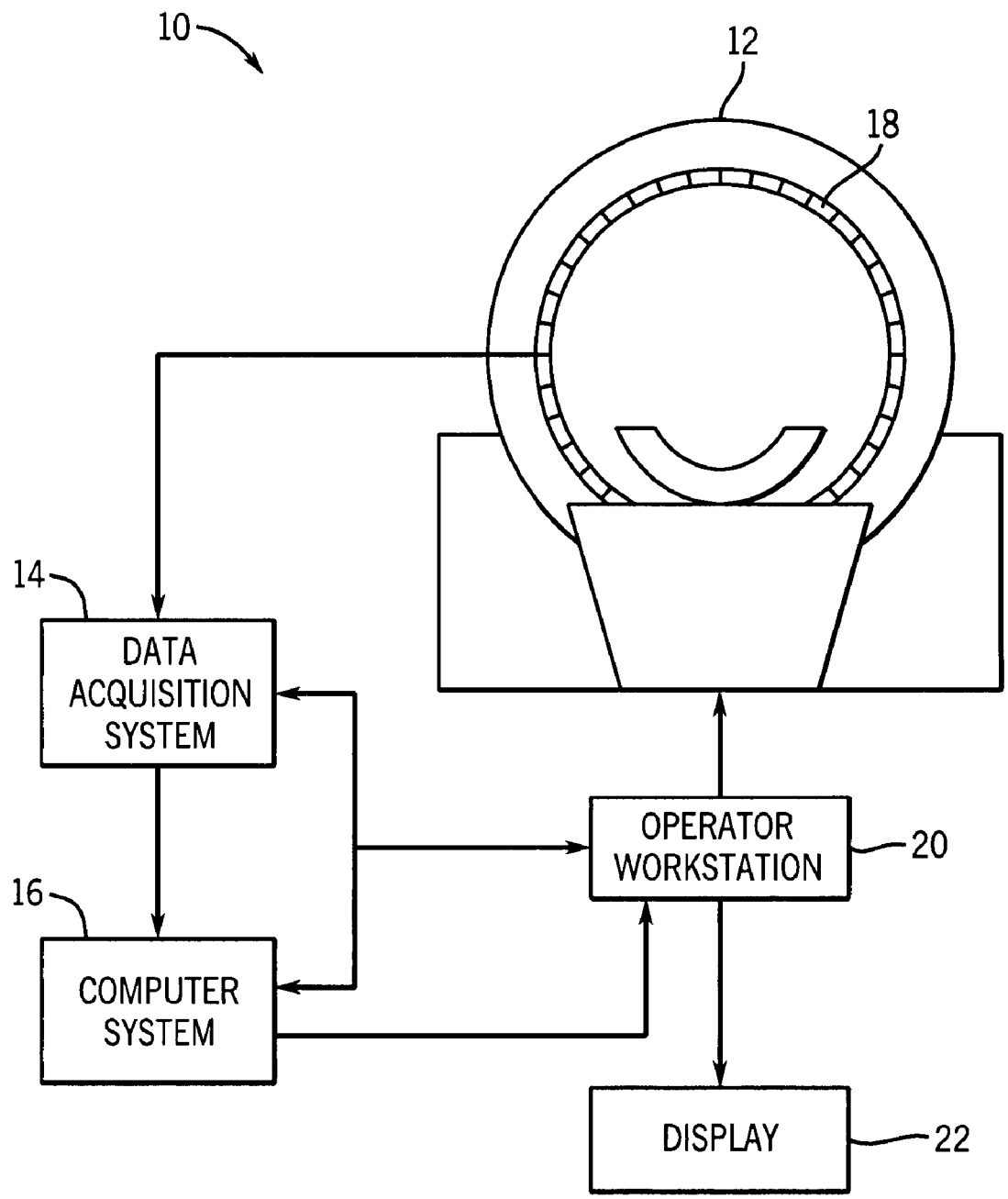
FIG. 1 is a diagrammatical illustration of an exemplary PET imaging system, in accordance with one embodiment of the present technique.

FIG. 1 illustrates diagrammatically an imaging system 10 for acquiring and processing image data. In the illustrated embodiment, system 10 is a positron emission tomography (PET) system designed to acquire tomographic data, to reconstruct the tomographic data into an image, and to process the image data for display and analysis in accordance with the present technique. The PET system 10 includes a detector assembly 12, a data acquisition system 14, and a computer system 16. The detector assembly 12 typically includes a number of detector modules (generally designated by reference numeral 18) arranged in one or more rings, as depicted in FIG. 1. The PET system 10 also includes an operator workstation 20 and a display 22. While in the illustrated embodiment, the data acquisition system 14, and the computer system 16 are shown as being outside the detector assembly 12 and the operator workstation 20, in certain other implementations, some or all of these components may be provided as part of the detector assembly 12 and/or the operator workstation 20. Each of the aforementioned components would be discussed in greater detail in the sections that follow.

In PET imaging, the patient is typically injected with a solution that contains a radioactive tracer. The solution is distributed and absorbed throughout the body in different degrees, depending on the tracer employed and the functioning of the organs and tissues. For instance, tumors typically process more glucose than a healthy tissue of the same type. Therefore, a glucose solution containing a radioactive tracer may be disproportionately metabolized by a tumor, allowing the tumor to be located and visualized by the radioactive emissions. In particular, the radioactive tracer emits particles known as positrons that interact with and annihilate complementary particles known as electrons to generate gamma rays. In each annihilation reaction, two gamma rays traveling in opposite directions are emitted. In a PET imaging system 10, the pair of gamma rays are detected by the detector assembly 12 configured to ascertain that two gamma rays detected sufficiently close in time are generated by the same annihilation reaction. Due to the nature of the annihilation reaction, the detection of such a pair of gamma rays may be used to determine the Line of Response (LOR) along which the gamma rays traveled before impacting the detector, allowing localization of the annihilation event to that line.

Referring again to FIG. 1, the data acquisition system 14 is adapted to read out signals generated in response to the gamma rays from the detector modules 18 of the detector assembly 12. For example, the data acquisition system 14 may receive sampled analog signals from the detector assembly 12 and convert the data to digital signals for subsequent processing by computer system 16.

Computer system 16 is coupled to the data acquisition system 14. The signals acquired by the data acquisition system 14 are provided to the computer system 16. The operator workstation 20 may be utilized by a system operator to provide control instructions to some or all of the described components and for configuring the various operating parameters that aid in data acquisition and image generation. A display 22 coupled to the operator workstation 20 may be utilized to observe the reconstructed image. It should be further noted that the operator workstation 20 and display 22 may be coupled to other output devices, which may include printers and standard or special purpose computer monitors. In general, displays, printers, workstations, and similar devices supplied with the PET system 10 may be local to the data acquisition components, or may be remote from these components, such as elsewhere within the institution or hospital, or in an entirely different location, linked to the image acquisition system via one or more configurable networks, such as the Internet, virtual private networks, and so forth.

As previously mentioned, an image of a targeted FOV that is less than the full scan FOV for the imaging system, such as the PET system 10, may be needed. For example, in cardiac imaging, a high resolution image of a small sub-region of the patient's anatomy may be desired. Those of ordinary skill in the art will appreciate that image reconstruction for this targeted FOV using iterative reconstruction techniques may be complicated by a variety of factors. One technique for targeted iterative reconstruction involves ignoring the signal from outside the targeted FOV, which may be referred to as "naïve reconstruction." This results in an anomalous image where the entire signal from outside the targeted FOV is assigned to the periphery of the targeted FOV. In other cases, an image of the full scan FOV may be reconstructed at high resolution from which the image for the targeted FOV may be extracted, which may be referred to as "brute-force reconstruction." These techniques for targeted iterative reconstruction, however, either inaccurately handle the signal from outside the targeted FOV or handle the signal in a computationally extensive manner.

Figure 2:
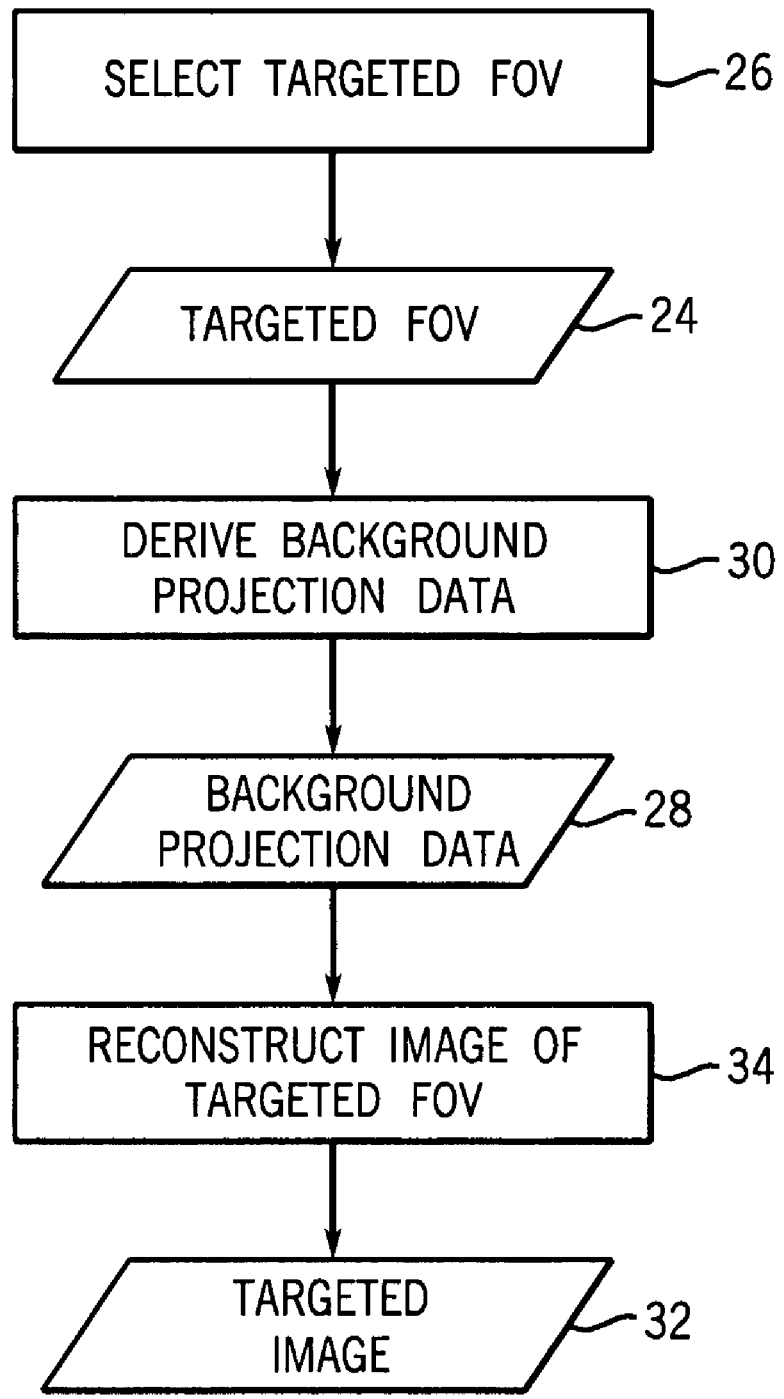
FIG. 2 is a flowchart depicting one technique for image reconstruction, in accordance with one aspect of the present technique.

To address these issues with iterative reconstruction of an image of a targeted FOV, an embodiment of the present technique provides a method for image reconstruction. Referring now to FIG. 2, a flow chart depicting a method associated with aspects of the present technique is presented. In the present technique, a targeted FOV 24 for a tomographic image may be selected, as depicted by block 26 of FIG. 2. As those of ordinary skill in the art will appreciate, the targeted FOV 24 of the tomographic image is less than or equal to the scan FOV of the imaging system 10. In general, the targeted FOV 24 may be selected by any suitable technique, including by a user, automatically, or semi-automatically. Next, background projection data 28 for the area outside the targeted FOV of the tomographic image may be derived, as depicted at block 30. Derivation of an exemplary background projection data 28 is described in more detail below with respect to FIG. 3. In general, the background projection data 28 may represent the activity from the area outside the targeted FOV 24. As will be appreciated, for transmission imaging (e.g., X-ray CT), the background projection data generally may represent attenuation of photon flux from the area outside the targeted FOV 24. Any suitable technique may be used to determine this background projection data 28. The background projection data 28 may then be used as an additional factor in the reconstruction of the targeted tomographic image 32 of the targeted FOV, as depicted at block 34. Reconstructing the targeted image 32 using the background projection data 28 may provide reduced artifacts and/or reduced reconstruction time as compared to alternative reconstruction techniques. Exemplary techniques for determining the background projection data 28 and for reconstructing the targeted image 32 will be discussed in the sections that follow.

Figure 3:
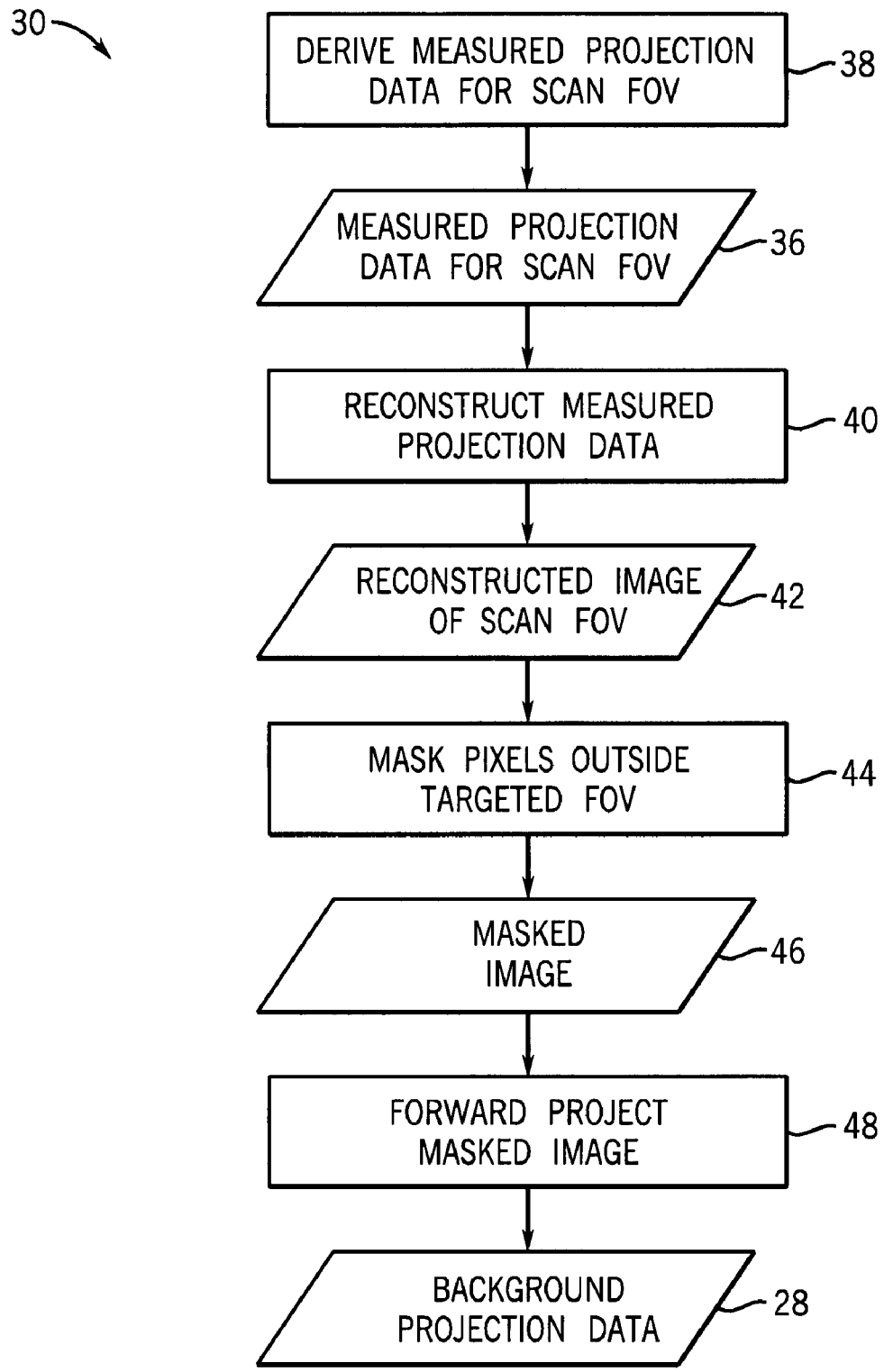
FIG. 3 is a flowchart depicting one technique for determining background projection data for an area outside a targeted FOV, in accordance with one aspect of the present technique.
Figure 4:
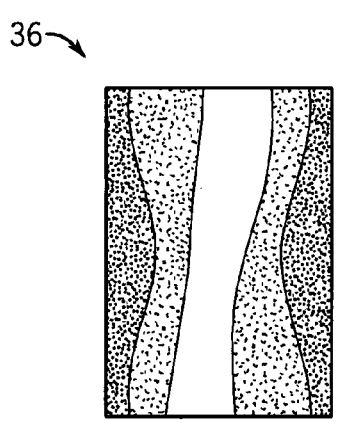
FIG. 4 is a diagrammatical view of a measured projection data for a scan FOV, in accordance with one aspect of the present technique.
Figure 5:
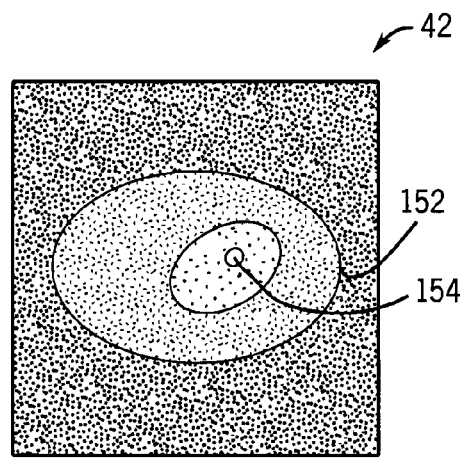
FIG. 5 is a diagrammatical view of a reconstructed image of the measured projection data of FIG. 4, in accordance with one aspect of the present technique.

Referring now to FIG. 3, a flowchart depicting an exemplary method for determining the background projection data 28 is presented. For determining the background projection data 28, measured projection data 36 for a scan FOV of the tomographic image may be derived at block 38. In general, the measured projection data 36 may contain activity from the full scan FOV. Referring now to FIG. 4, exemplary measured projection data 36 for a scan FOV is represented as a sinogram. Returning to FIG. 3, this measured projection data 36 may be reconstructed at block 40 to obtain a reconstructed image 42 of the scan FOV. An exemplary reconstructed image 42 of the scan FOV is depicted on FIG. 5. In the reconstructed image 42 of FIG. 5, the subject imaged is represented by numeral 152, and the feature of interest is represented by number 154. As those of ordinary skill in the art will appreciate, any suitable reconstruction technique may be utilized to obtain this reconstructed image 42 of the scan FOV, including analytical reconstruction and iterative reconstruction algorithms. For example, full convergence of an iterative reconstruction algorithm may not be necessary for the image reconstruction of the scan FOV because only a reasonable estimate of the background projection data may be needed. In other words, an image generated with less number of iterations through an iterative reconstruction algorithm may be needed to obtain the background projection data 28 than would be required to accurately reconstruct a reliable image of the scan FOV. In another example, the pixel grid utilized for this reconstruction of the scan FOV may be larger, than the pixel grid used for reconstruction of the targeted FOV.

Figure 6:
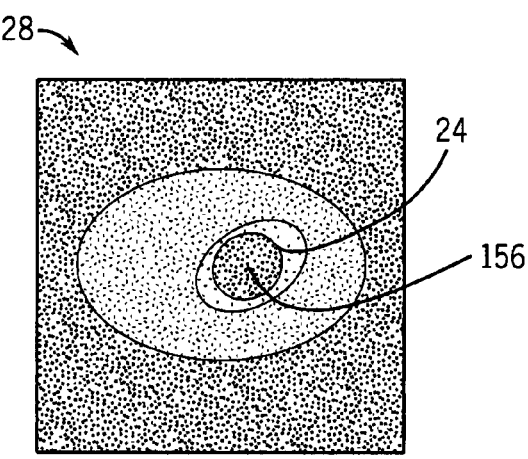
FIG. 6 is a diagrammatical view of the reconstructed image of FIG. 5 with the pixels corresponding to the targeted FOV masked, in accordance with one aspect of the present technique.
Figure 7:
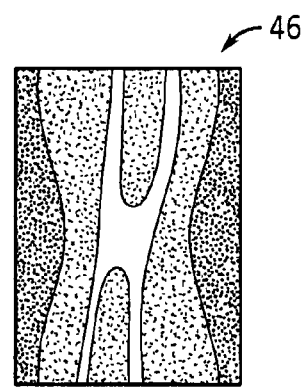
FIG. 7 is a diagrammatical view of a forward projection of the reconstructed image of FIG. 6; in accordance with one aspect of the present technique.

Once the reconstructed image 42 for the scan FOV has been obtained at block 40, pixels outside the targeted FOV may be masked out in the reconstructed image 42, at block 44. By way of example, masking out the pixels may include zeroing the pixels in the reconstructed image 42 that are inside the targeted FOV 24. An exemplary masked image 46 is depicted on FIG. 6. In the masked image 46 of FIG. 6, the targeted FOV is represented by numeral 24, and the masked pixels are represented by number 156. To obtain the background projection data 28 for the area outside the targeted FOV 24, the masked image 46 may be forward projected, at block 48. As previously mentioned, the background projection data 28 generally may represent the activity outside the targeted FOV. Referring now to FIG. 7, exemplary background projection data 28 is depicted as a sinogram.

As previously mentioned, the background projection data 28 may be used as an additional factor in the reconstruction of a targeted image 32. As those of ordinary skill in the art will appreciate, any suitable reconstruction technique may be used to reconstruct the targeted image, including a variety of iterative reconstruction algorithms. One technique for using the background projection data 28 as an additional factor in the reconstruction of the targeted image 32 includes pre-correcting the measured projection data 36 for the scan FOV. Another suitable technique includes utilizing an attenuated background projection data 28 as an additional additive correction term for a projection data estimate from the forward projected image estimate.

Figure 9:
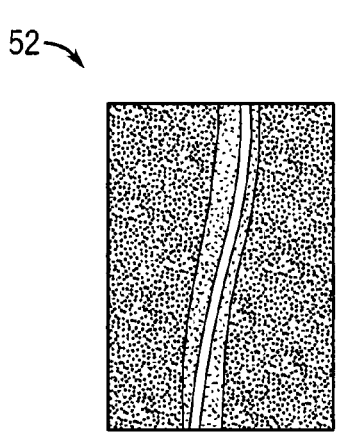
FIG. 9 is a diagrammatical view of an exemplary targeted projection data representing activity from inside the targeted FOV.
Figure 8:
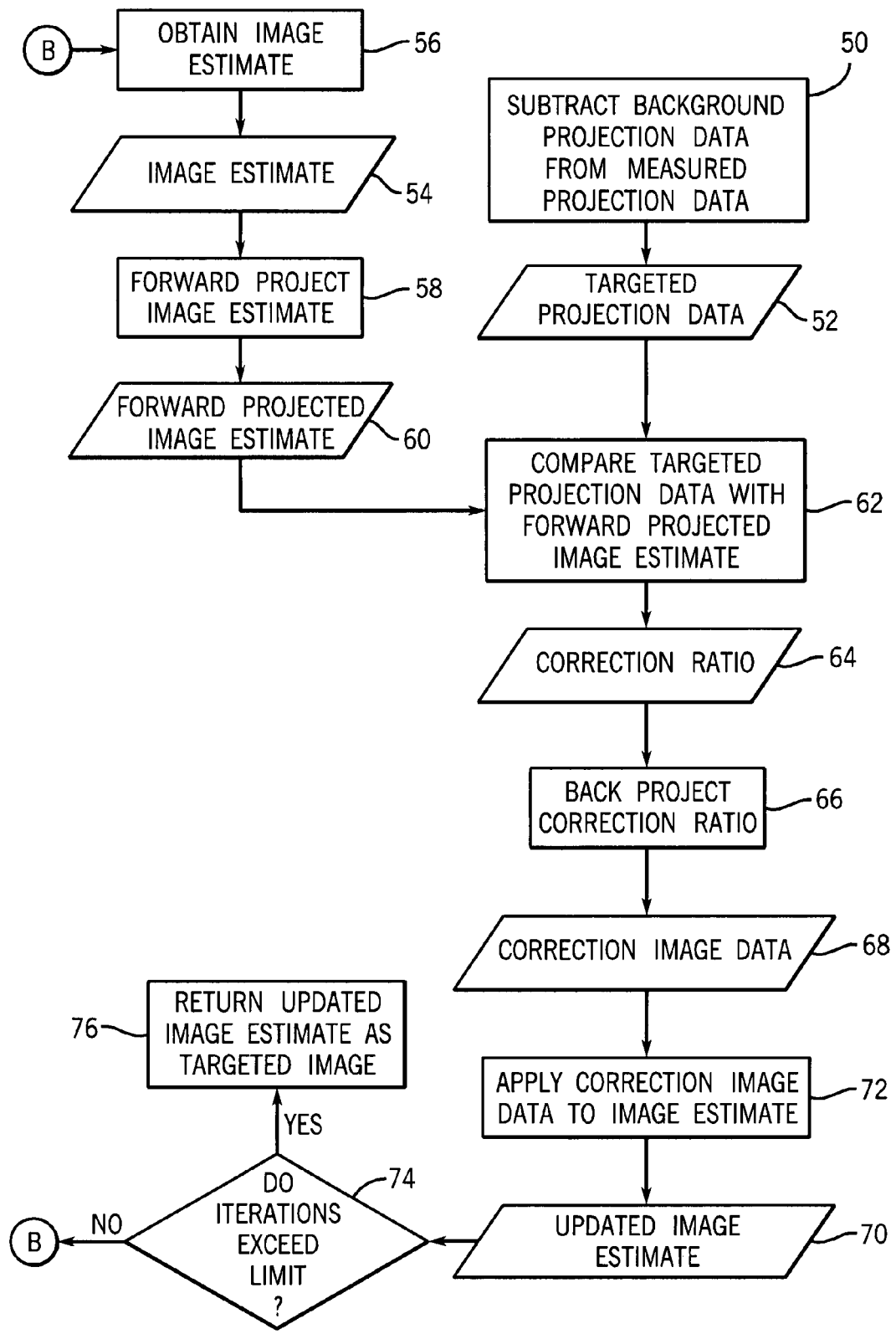
FIG. 8 is a flowchart depicting one technique for utilizing background projection data in an iterative reconstruction algorithm.

Referring now to FIG. 8, a flowchart depicting this pre-correction technique is illustrated. In the illustrated embodiment, the measured projection data 36 for the scan FOV may be pre-corrected by subtracting the background projection data 28 from the measured projection data 36, as depicted in block 50. As a result of this subtraction, targeted projection data 52 for the targeted FOV is obtained. In general, the targeted projection data 52 may represent activity inside the targeted FOV. Referring now to FIG. 9, exemplary targeted projection data 52 is illustrated as a sinogram. As will be appreciated, the measured projection data 36 may also be corrected for photon scatter, presence of random events, scanner dead time, scanner detector efficiency, scanner geometric effects, and radiopharmaceutical decay.

Returning to FIG. 8, an image estimate 54 for the targeted FOV may be obtained, as depicted at block 56. As will be appreciated, this image estimate 54 may take any of a number of forms and may include a uniform image or an estimate obtained from a reconstruction technique, such as filtered back projection. This image estimate 54 may then be forward projected, as depicted in block 58, to the projection plane to obtain a forward projected image estimate 60. In addition, attenuation factors may also be applied to the forward projected image estimate 60.

Figure 10:
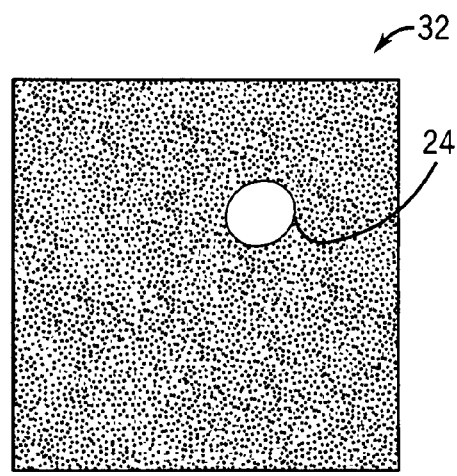
FIG. 10 is a diagrammatical view of a reconstructed image for the targeted FOV.

This forward projected image estimate 60 may then be compared to the targeted projection data 52, as depicted at block 62. For example, this comparison may include taking the ratio of the targeted projection data 52 and the forward projected image estimate 60 to obtain a correction ratio 64. In addition, attenuation factors may also be applied to the correction ratio 64. As depicted at block 66, the correction ratio 64 may be back projected to obtain correction image data 68. An updated estimated image 70 may then be obtained by applying the correction image data 68 to the image estimate 54, as depicted at block 72. In one embodiment, the corrected image data 68 and the image estimate 54 are multiplied to obtain the updated image estimate 70 for the targeted FOV. As will be appreciated, the updated image estimate 70 is the image estimate 54 to be used in the next iteration of the update equation. As depicted at block 74, it is determined whether the number of iterations for generating the image for the targeted FOV exceeds a threshold value. If the number of iterations exceeds the threshold value, the updated image estimate 70 is returned, as depicted at block 76 as the targeted image 32. Alternatively, rather than using a threshold value, it may be determined whether convergence between the image estimate 54 and the updated image estimate 70 has reached a desired level. Otherwise, blocks 50 to 74 are performed iteratively. An exemplary targeted image 32 is depicted on FIG. 10. In the targeted image 32 of FIG. 10, the targeted FOV is represented by numeral 24.

As will be appreciated by those of ordinary skill in the art, the embodiment illustrated by FIG. 8 may be implemented utilizing the Ordered Subsets Expectation Maximization (OSEM) algorithm. While the OSEM algorithm is shown below, exemplary embodiments of the present technique may be implemented using any suitable iterative reconstruction update equation. Accordingly, the embodiment illustrated by FIG. 8 may be described by equation (1) as follows:

$$\lambda_j^{k,m+1} = \frac{\lambda_j^{k,m}}{\sum_{i \in S_m} P_{i,j} A_i} \sum_{i \in S_m} P_{i,j} \frac{y_i - t_i^{bkg} - r_i - s_i}{\sum_{j'} P_{i,j'} \lambda_{j'}^{k,m}} \quad (1)$$

Wherein:

$\lambda$ refers to an image estimate, and $\lambda_j^{k,m}$ refers to the image estimate for pixel j at the $k^{th}$ iteration and the $m^{th}$ subset of LORs;

y refers to the measured projection data for the scan FOV, and $y_i$ refers to the measured projection data detected by the $i^{th}$ LOR;

$r_i$ refers to the random coincidences detected by the $i^{th}$ LOR;

$s_i$ refers to the scatter coincidences detected by the $i^{th}$ LOR;

$A_i$ refers to the attenuation factor along the $i^{th}$ LOR;

$P_{i,j}$ refers to the projection matrix that determines the probability that activity from pixel j is detected by $i^{th}$ LOR;

$t_i^{bkg}$ refers to the attenuated background projection data detected by the $i^{th}$ LOR; and $S_m$ refers to the $m^{th}$ subset of LORs.

As previously mentioned, another suitable technique includes utilizing an attenuated background projection data 28 as an additional additive correction term for the forward projected image estimate 60. This technique may be referred to as a "corrections-in-the-loop" technique.

Figure 11:
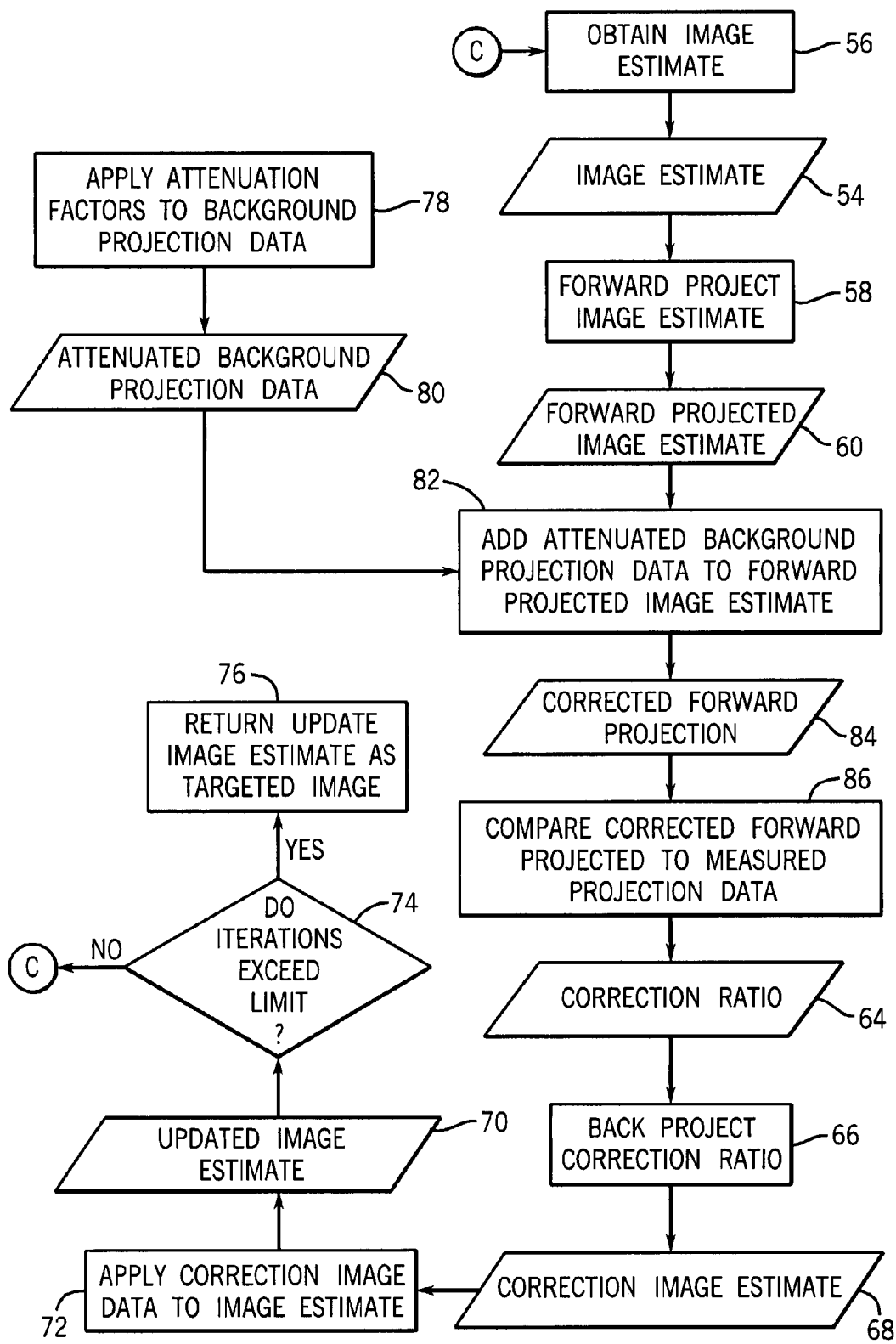
FIG. 11 is a flowchart depicting another technique for utilizing background projection data in an iterative reconstruction algorithm.

Referring now to FIG. 11, a flowchart depicting this corrections-in-the-loop technique is illustrated. In the illustrated embodiment, an image estimate 54 for the targeted FOV may be obtained, as depicted at block 56. As will be appreciated, this image estimate 54 may take any of a number of forms and may include a uniform image or an estimate obtained from a reconstruction technique, such as filtered back projection. This image estimate 54 may then be forward projected, as depicted in block 58, to the projection plane to obtain a forward projected image estimate 60. In addition, attenuation factors may also be applied to the forward projected image estimate 60.

In addition, as depicted at block 78, attenuation factors may be applied to the background projection data 28 to obtain attenuated background projection data 80. An exemplary technique for determining the background projection data was discussed above with respect to FIG. 3. This background projection data 28 may be then added to the forward projected image estimate 58 as an additive corrective term, as depicted at block 82 to obtain a corrected forward projection 84. As will be appreciated, the forward projected image estimate 60 may also be corrected for photon scatter, presence of random events, scanner dead time, scanner detector efficiency, scanner geometric effects, and radiopharmaceutical decay.

This corrected forward projection 84 then may be compared to the measured projection data 36, as depicted at block 86. For example, this comparison may include taking the ratio of the measured projection data 50 and the corrected forward projection 84 to obtain a correction ratio 64. In addition, attenuation factors may be applied to the correction ratio 64. As depicted at block 66, the correction ratio 64 may be back projected to obtain correction image data 68. An updated estimated image 70 may then be obtained by applying the correction image data 68 to the image estimate 54, as depicted at block 72. In one embodiment, the corrected image data 68 and the image estimate 54 are multiplied to obtain the updated image estimate 70 for the targeted FOV. As will be appreciated, the updated image estimate 70 is the image estimate 54 to be used in the next iteration. As depicted at block 74, it is determined whether the number of iterations for generating the image for the targeted FOV exceeds a threshold value. If the number of iterations exceeds the threshold value, the updated image estimate 70 is returned, as depicted at block 76, as the targeted image 32. Alternatively, rather than using a threshold value, it may be determined whether convergence between the image estimate 54 and the updated image estimate 70 has reached a desired level. Otherwise, the technique of FIG. 11 starting at block 56 is performed iteratively.

As will be appreciated by those of ordinary skill in the art, the embodiment illustrated by FIG. 11 may be implemented utilizing the Ordered Subsets Expectation Maximization (OSEM) algorithm. While the OSEM algorithm is shown below, exemplary embodiments of the present technique may be implemented using any suitable iterative reconstruction update equation. Accordingly, the embodiment illustrated by FIG. 11 may be described by equation (2) as follows:

$$\lambda_j^{k,m+1} = \frac{\lambda_j^{k,m}}{\sum_{i \in S_m} P_{i,j} A_i} \sum_{i \in S_m} P_{i,j} \frac{A_i y_i}{\sum_{j'} A_i P_{i,j'} \lambda_{j'}^{k,m} + t_i^{bkg} + r_i + s_i} \quad (2)$$

Wherein:

$\lambda$ refers to an image estimate, and $\lambda_j^{k,m}$ refers to the image estimate for pixel j at the $k^{th}$ iteration and the $m^{th}$ subset of LORs;

y refers to the measured projection data for the scan FOV, and $y_i$ refers to the measured projection data detected by the $i^{th}$ LOR;

$r_i$ refers to the random coincidences detected by the $i^{th}$ LOR;

$s_i$ refers to the scatter coincidences detected by the $i^{th}$ LOR;

$A_i$ refers to the attenuation factor along the $i^{th}$ LOR;

$P_{i,j}$ refers to the projection matrix that determines the probability that activity from pixel j is detected by $i^{th}$ LOR;

$t_i^{bkg}$ refers to the attenuated background projection data detected by the $i^{th}$ LOR; and $S_m$ refers to the $m^{th}$ subset of LORs.

As will be appreciated by those of ordinary skill in the art the exemplary techniques described herein are applicable to both static reconstruction, as well as motion compensated reconstruction, such as motion compensated PET reconstruction. By way of example, the background projection data 28 may also be used as an additional factor in a motion compensated reconstruction. In motion compensated reconstruction, the reconstruction is applied to four dimensions wherein the fourth dimension is time gating. By way of example, multiple gates of data are acquired based on time dependent gating, for example, on respiratory gating or cardiac gating. However, while the multiple gates of data are time dependent, the background projection data 28 derived for use in the motion compensated reconstruction need not be time dependent. For example, a low resolution, motion uncompensated image may be used to derive the background projection data. The motion uncompensated image may be reconstructed from a sum of all the projection gates of data. From this motion uncompensated image, the background projection data 28 may be derived, for example, by masking the pixels within the targeted FOV and then forward projecting the masked image, in accordance with the exemplary embodiment of FIG. 3. To obtain the background projection data for each of the projection gates, the background projection data 28 may be scaled by the relative acquisition times of each corresponding projection gate.

Exemplary embodiments of the present technique may be implemented using any suitable motion compensated reconstruction update equation. An exemplary embodiment of the present technique for motion compensated reconstruction may be represented by equation (3) as follows:

$$\lambda_j^{(k,m+1)} = \frac{f_j^{(k,m)}}{\sum_{i \in S_m} \sum_{g=1}^{G} A_i^g w_{j'}^g P_{ij}^g} \sum_{i \in S_m} \sum_{g=1}^{G} A_i^g w_{j'}^g P_{ij}^g \frac{y_i^g}{\sum_{j'} A_i^g P_{ij'}^g w_{j'}^g \lambda_{j'}^{(k,m)} + \frac{T_g t_i^{bkg}}{T_{period}} + s_i^g + r_i^g} \quad (3)$$

Wherein:

$\lambda$ refers to an image estimate, and $\lambda_j^{k, m}$ refers to the image estimate for pixel j at the $k^{th}$ iteration and the $m^{th}$ subset of LORs;

$y_i^g$ refers to the measured projection data detected by the $i^{th}$ LOR for gate g;

$r_i^g$ refers to the random coincidences detected by the $i^{th}$ LOR for gate g;

$s_i^g$ refers to the scatter coincidences detected by the $i^{th}$ LOR for gate g;

$A_i^g$ refers to the attenuation factor along the $i^{th}$ LOR for gate g;

$P_{i,j}$ refers to the projection matrix that determines the probability that activity from pixel j is detected by the $i^{th}$ LOR for gate g;

$t_i^{bkg}$ refers to the attenuated background projection data detected by the $i^{th}$ LOR;

$T_g$ is the acquisition time of the projection data for gate g;

$T_{period}$ is the period of the respiratory or cardiac cycle;

$w^g$ is the deformation operator (motion) for gate g;

$S_m$ refers to the $m^{th}$ subset of LORs; and

G refers to the number of gates acquired over the respiratory or cardiac cycle.

As previously discussed, the exemplary techniques of the present technique provide a method for the iterative reconstruction of an image of a targeted FOV that is less than the full scan FOV. As described above, reconstruction of a targeted image (such as targeted image 32) in accordance with embodiments of the present technique may provide reduced artifacts as compared to alternative reconstruction techniques. Artifacts, however, may appear in the targeted image due to a variety of factors.

Figure 12:
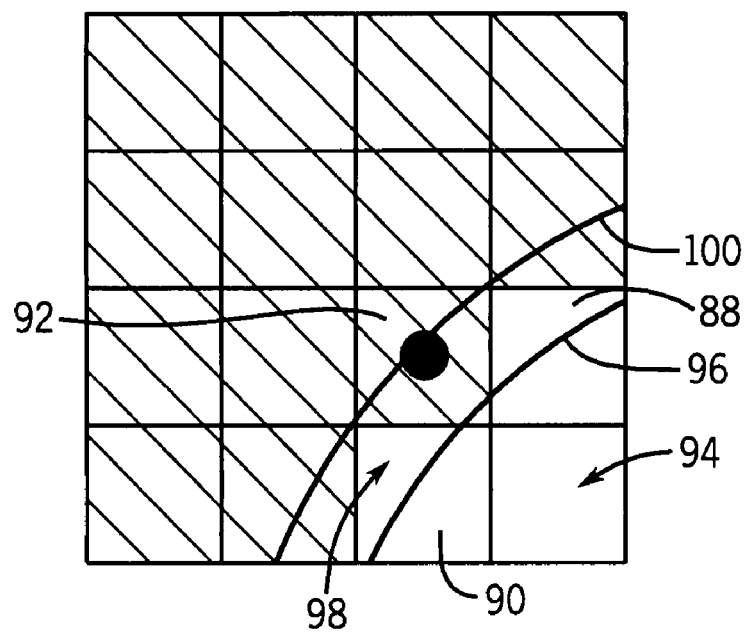
FIG. 12 is a diagrammatical view of an expanded targeted FOV, in accordance with one aspect of the present technique.

In one instance, pixels that straddle the targeted FOV may result in artifacts on the edges of the targeted image. By way of example, these artifacts may occur when the background projection data 28 representing activity outside the targeted FOV is subtracted from the measured projection data 36, in accordance with aspects of the present technique. As illustrated by FIG. 12, pixels 88, 90, 92 are shown straddling the targeted FOV 94. The edge of the targeted FOV is represented on FIG. 12 by numeral 96. In the illustrated embodiment, the targeted FOV 94 is defined to include all pixels having a center within the targeted FOV 94. Accordingly, pixels 88, 90 are shown within the targeted FOV 94. Pixel 92, however, does not have a center within the targeted FOV 94 and, thus, is not shown as within the targeted FOV 94. Because pixel 92 extends into the targeted FOV 94 while not being defined as within the targeted FOV 94, artifacts may occur in the reconstructed image. For instance, pixel 92 will not be masked during determination of the background projection data 28, in accordance with certain aspects of the present technique.

To address this issue, the targeted FOV 94 may be expanded so that any pixel extending into the targeted FOV 94, such as pixel 92, may be considered within the expanded targeted FOV 98. For example, the targeted FOV 94 may be expanded beyond the targeted FOV that was originally identified. By way of example, the expanded targeted FOV may be defined as targeted FOV plus a buffer zone 98. The edge of the buffer zone 98 is represented on FIG. 12 by numeral 100. In one embodiment, this buffer zone 98 may expand beyond the original targeted FOV by a distance equal to sqrt(½) of a pixel width. As illustrated on FIG. 12, the targeted FOV 94 may be expanded so that pixel 92 that previously straddled the targeted FOV is inside the buffer zone 98.

Figure 13:
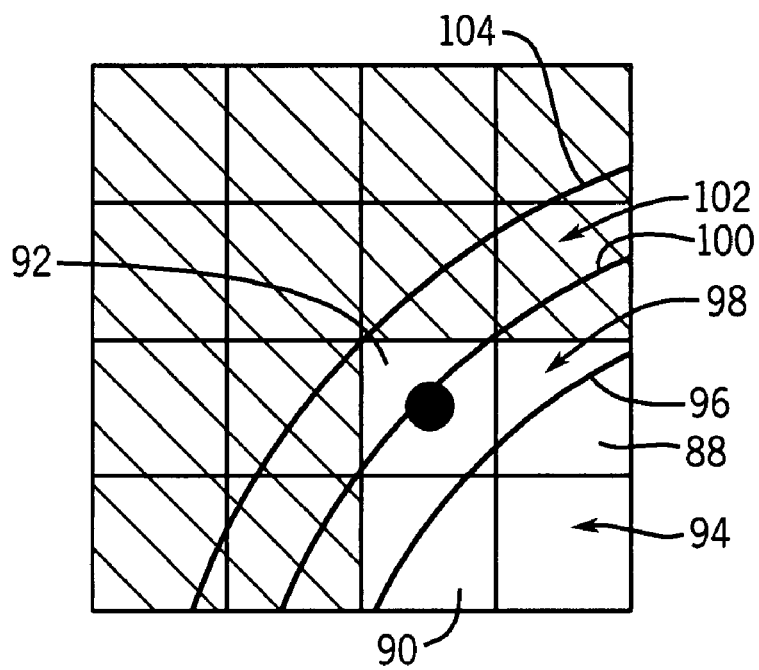
FIG. 13 is a diagrammatical view of an expanded targeted FOV, in accordance with one aspect of the present technique.

In another embodiment, the targeted FOV 94 may be expanded so that the entire pixel 92 (and not just the center) is contained within a second buffer zone 102 for the targeted FOV 94. The second buffer zone 102 may extend beyond the first buffer zone 98 by a distance of sqrt(½) of a pixel width. The edge of the second buffer zone 102 is represented on FIG. 13 by numeral 102. Including the entire pixel 92 within the expanded targeted FOV may ensure, for example, that the pixel 92 will be represented in the targeted reconstruction. As will be appreciated, the targeted image may be constructed for this expanded targeted FOV 98, in accordance with an embodiment of the present technique. The portion of the targeted image that extends beyond the original targeted FOV 94 may be trimmed so that the final reconstructed image is for the targeted FOV 94. For example, the reconstructed portion of buffer zone 98 and second buffer zone 102 may be trimmed from the targeted image.

The targeted FOV may also be expanded for motion compensated reconstruction. As those of ordinary skill in the art will appreciate, projection data from the different gates may be reconstructed independently and subsequently registered and combined. Alternatively, the motion estimates, on a voxel-by-voxel basis, can be incorporated into an iterative reconstruction algorithm that uses all the projection data. In either case, motion estimates are generally made on a voxel-by-voxel basis. However, motion (such as cardiac or respiratory motion) may cause voxels at the edge of the targeted FOV to move in and out of the targeted FOV. Accordingly, the targeted FOV may be expanded to include a buffer zone. The buffer zone may include the range of motion of all voxels inside the targeted FOV. After image reconstruction, this buffer zone may be trimmed from the reconstructed image.

In addition, artifacts in the targeted image may also be due to pixel discontinuities in the reconstructed image of the scan FOV that may forward project as streaks through an image of the targeted FOV. To address this issue, projection data filtering may be applied after a forward projection step, such as after block 58 on FIGS. 8 and 11. In one exemplary embodiment, the projection data filtering may be based on the relative size of the scan FOV pixel versus the element width for the projection data.

While the present discussion does not reference image shifts and rotations applied during the course of image reconstruction, those of ordinary skill in the art will appreciate that these shifts and rotations may be applied in accordance with aspects of the present technique. For example, because the targeted reconstruction coordinates are defined with respect to the output coordinate system, which may be rotated with respect to, for example, the PET gantry, the measured projection data for the scan FOV 36 may be reconstructed (block 40) and forward projected (block 48) with the shift and rotation parameters applied. In one embodiment, the shift and rotation parameters may be ignored in the reconstruction of the measured projection data (block 40) while the definition of the targeted FOV includes the shift and rotation parameters. In another embodiment, the shift and rotation parameters may be applied to the reconstruction of the measured projection data (block 40). In both instances, the forward projection (block 48) should match the reconstruction of the measured projection data (block 40).

In addition, while the present technique may provide reduced reconstruction times as compared to alternative reconstruction techniques (such as the brute-force reconstruction), the present technique may provide slower reconstruction times in certain instances. As previously mentioned, the brute-force methodology reconstructs an image for the full scan FOV and then extracts the targeted image for the targeted FOV from this reconstructed image. However, because the present technique involves multiple reconstruction operations, the present technique may provide slower reconstruction than the brute-force method, in certain instances. To address this issue, an embodiment of the present technique provides a method for selecting a reconstruction methodology. In general, this method compares the complexity of the reconstruction methods to determine the most efficient method. In the present example, the complexity of the reconstruction methods may be compared by comparing the number of pixels in the reconstructed images. Accordingly, the number of pixels for each reconstruction method should be determined.

By way of example, a scan FOV may have a diameter of SFOV, a targeted FOV may have a diameter of TFOV, and a targeted reconstruction of $N_T^2$ pixels at the targeted FOV. In this illustration, the brute-force reconstruction may scale the $N_T$ pixel dimensions by a factor of SFOV/TFOV. As such, for the brute-force reconstruction, the number of pixels may be represented with equation 4 as follows:

$$\left(\frac{N_T SFOV}{TFOV}\right)^2 \quad (4)$$

wherein $N_T$ is the size of the pixel grid for the targeted reconstruction, SFOV is the diameter of the scan FOV, and TFOV is the diameter of the targeted FOV.

For the present technique using the background projection data 28, there may be two reconstructions. First, during the derivation of the background projection data 28, the measured projection data 36 may be reconstructed to obtain a reconstructed image 42 of the full scan FOV. The number of pixels for this "first reconstruction" is size of the pixel grid ($N_F$) selected for the reconstruction of the full scan FOV. As such, the number of pixels for this first reconstruction is $N_F^2$. In general, the number of pixels for the targeted reconstruction is the square of the pixel grid (or $N_T^2$). However, as previously discussed, the targeted FOV may be expanded to include a buffer zone. Accordingly, the number of pixels for this second reconstruction may be represented by equation (5) as follows:

$$N_T * \left(1 + \frac{2\sqrt{2}\, SFOV}{N_F TFOV}\right) \quad (5)$$

wherein $N_T$ is the size of the pixel grid for the targeted reconstruction, SFOV is the diameter of the scan FOV, and TFOV is the diameter of the targeted FOV. Accordingly, the number of pixels for this second reconstruction may be the square of this reconstruction. By combining the number of pixels for the first reconstruction and the second reconstruction, the number of pixels for the present technique may be represented by equation (6) as follows:

$$N_F^2 \left[ N_T * \left(1 + \frac{2\sqrt{2}\, SFOV}{N_F TFOV}\right) \right]^2 \quad (6)$$

wherein $N_T$ is the size of the pixel grid for the targeted reconstruction, SFOV is the diameter of the scan FOV, and TFOV is the diameter of the targeted FOV.

In one embodiment, to compare the complexity of the reconstruction methodologies, the number of pixels for the two reconstructions may be compared with the following equation. Based on this comparison, a reconstruction method may be selected. As those of ordinary skill in the art will appreciate, each design may have a crossover point wherein the brute-force method may have faster reconstruction times than the present technique. In one embodiment, the crossover point may be represented by equation (7) as follows:

$$\text{Crossover } TFOV = \frac{N_F \sqrt{1 + \frac{N_F^2}{N_T^2} - 2\sqrt{2}}}{N_F\left(1 + \frac{N_F^2}{N_T^2}\right)} SFOV \quad (7)$$

By way of example, the following Table illustrates exemplary crossover points for a scan FOV having a diameter of 70 centimeters:

TABLE 1

| Parameters | Crossover TFOV |
|---|---|
| $N_T = 128, N_F = 128$ | 49 cm |
| $N_T = 128, N_F = 64$ | 60 cm |
| $N_T = 256, N_F = 64$ | 65 cm |

As will be appreciated, the brute-force method may have faster reconstruction times for targeted FOVs having a diameter greater than the crossover TFOV calculated with the above equation.

As noted above, while specific reference is made in the present discussion to a PET system 10, it should be appreciated that the present technique is not intended to be limited to these or to any specific type of imaging system or modality. In general, the present technique may be used for image reconstruction with imaging modalities that use line integral projection tomography reconstruction. Examples include PET imaging, single photon emission computed tomography (SPECT) imaging, and x-ray computed tomography (CT) imaging. Such imaging modalities are particularly suited for reconstructing high resolution images of a targeted FOV that is less than the scan FOV for the imaging system.

Figure 14:
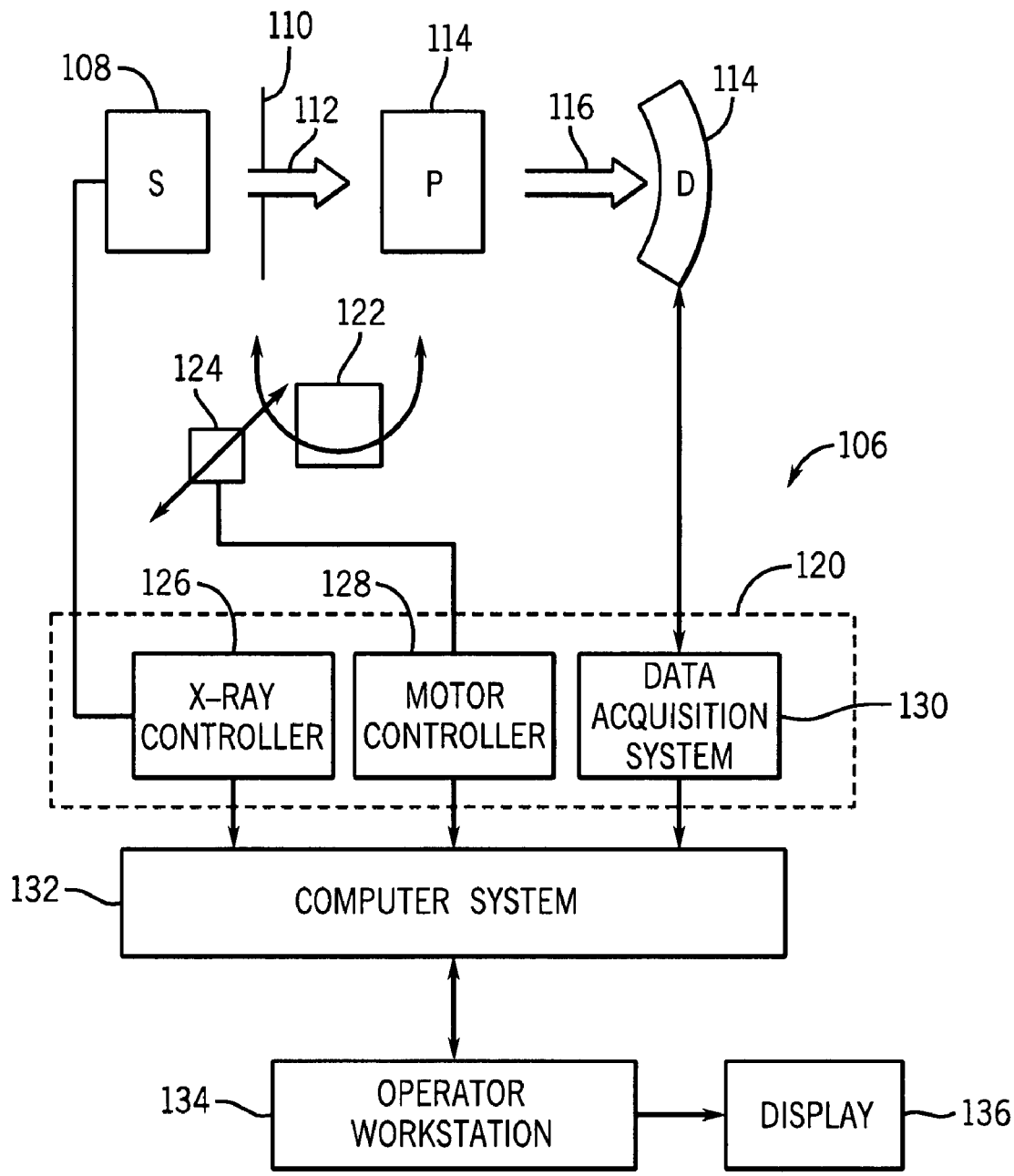
FIG. 14 is a diagrammatical illustration of an exemplary CT imaging system, in accordance with one embodiment of the present technique.

FIG. 14 illustrates diagrammatically another imaging system 106 for acquiring and processing image data. In the illustrated embodiment, system 106 is a computed tomography (CT) system designed both to acquire original image data, and to process the image data for display and analysis. In the embodiment illustrated in FIG. 14, CT system 106 includes a source of X-ray radiation 108 (such as an X-ray tube) positioned adjacent to a collimator 110. Collimator 110 permits a stream of radiation 112 to pass into a region in which a subject, such as a human patient 114 is positioned. A portion of the radiation 116 passes through or around the subject and impacts a detector array, represented generally at reference numeral 118.

X-ray source 108 and detector array 118 are coupled to the system control 120. In general, system controller 120 commands operation of the CT system 106 to execute examination protocols and to process acquired data. In the present context, system controller 120 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 14, system controller 120 is coupled to a linear positioning subsystem 122 and rotational subsystem 124. The rotational subsystem 122 enables the X-ray source 106, collimator 108 and the detector 118 to be rotated one or multiple turns around the patient 114. It should be noted that the rotational subsystem 124 might include a gantry. Thus, the system controller 120 may be utilized to operate the gantry. The linear positioning subsystem 122 enables the patient 114, or more specifically a patient table, to be displaced linearly. Thus, the patient table may be linearly moved within the gantry to generate images of particular areas of the patient 114.

Additionally, the system controller 120 comprises an X-ray controller 126, a motor controller 128, and a data acquisition system 130. In general, the X-ray controller 126 may be configured to provide power and timing signals to the X-ray source 116. The motor controller 128 may be utilized to control the movement of the rotational subsystem 124 and the linear positioning subsystem 122. In this exemplary embodiment, the detector array 118 is coupled to the system controller 120, and more particularly to the data acquisition system 130. The data acquisition system 130 receives data collected by readout electronics of the detector array 118. The data acquisition system 130 typically receives sampled analog signals from the detector array 118 and converts the data to digital signals for subsequent processing by a computer system 132.

The computer system 132 is typically coupled to the system controller 120. The data collected by the data acquisition system 130 may be transmitted to the computer system 132. Computer system 132 may include memory components for storing data that may be utilized by exemplary CT system 106. Also the computer system 132 is configured to receive commands and scanning parameters from an operator via an operator workstation 134 typically equipped with a keyboard and other input devices. An operator may control the CT system 106 via the input devices. Thus, the operator may observe the reconstructed image and other data relevant to the system from computer system 132, initiate imaging, and so forth. Additionally, the image may be printed by a printer which may be coupled to the operator workstation 134.

A display 136 coupled to the operator workstation 134 may be utilized to observe the reconstructed image and to control imaging. The display 136 may also be connected to the computer system 132, either directly or via the operator workstation 134. It should be further noted that the computer system 132 and operator workstation 134 may be coupled to other output devices, which may include standard, or special purpose computer monitors and associated processing circuitry. One or more operator workstations 134 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

In contrast to PET and SPECT imaging, X-ray CT imaging depends on the transmission of X-rays through the object. Despite this contrast, the present technique may be applied to X-ray CT iterative reconstruction. The standard imaging equation for X-ray CT is given by equation (8) as follows:

$$\hat{y}_i = b_i \cdot \exp\left(-\sum_j P_{i,j} \mu_j\right) + S_i \tag{8}$$

Wherein:

$\hat{y}_i$ refers to the mean photon flux detected at the detector i in the presence of the object;

$b_i$ refers to the photon flux that would have been detected at the detector i in the absence of the object;

$\mu_j$ refers to the linear attenuation coefficient of the object for the pixel j;

$S_i$ refers to the scatter flux detected at the detector i; and $P_{i,j}$ refers to the effective intersection length of the LOR i with pixel j X-ray imaging is often performed in the presence of an anti-scatter grid, resulting in $S_i=0$. However, in the absence of an anti-scatter grid, $S_i$ can be large enough not to be ignored and can be estimated by other algorithmic means. Accordingly, in a manner similar to PET and SPECT, the data can be pre-corrected for scatter or scatter correction can be incorporated into the reconstruction loop.

CT reconstruction may be implemented using any of a variety of suitable reconstruction algorithms. As will be appreciated by those of ordinary skill in the art, CT reconstruction may utilize Maximum Likelihood Transmission (MLTR) algorithm. An exemplary MLTR algorithm for the pre-correction technique and the corrections in the loop technique that do not implement the present technique are given by equations (9) and (10), respectively:

$$\mu_j^{k,m+1} = \mu_j^{k,m} + \frac{\sum_{i \in S_m} P_{i,j}(\hat{y}_i - y_i - S_i)}{\sum_{i \in S_m} P_{i,j} \cdot \left[\sum_{j'} P_{i,j'}\right] \cdot \hat{y}_i} \quad (9)$$

$$\mu_j^{k,m+1} = \mu_j^{k,m} + \frac{\sum_{i \in S_m} P_{i,j} \cdot \frac{(\hat{y}_i - S_i)}{\hat{y}_i} \cdot (\hat{y}_i - y_i)}{\sum_{i \in S_m} P_{i,j} \cdot \left[\sum_{j'} P_{i,j'}\right] \cdot (\hat{y}_i - S_i) \cdot \left(1 - \frac{y_i S_i}{\hat{y}_i^2}\right)} \quad (10)$$

Wherein:

$\mu$ refers to an image estimate, and $\mu_j^{k,m}$ refers to the image estimate for pixel j at the $k^{th}$ iteration and the $m^{th}$ subset of LORs;

$P_{i,j}$ refers to the effective intersection length of the LOR i with pixel j;

$S_i$ refers to the scatter flux detected at the detector i;

$\hat{y}_i$ refers to the mean photon flux detected at the detector i in the presence of the object;

$y_i$ refers to the measured projection data detected by the $i^{th}$ LOR; and $S_m$ refers to the $m^{th}$ subset of LORs.

Exemplary embodiments of the present technique may be implemented for use with CT reconstruction. As previously discussed with respect to FIG. 2, an exemplary embodiment of the present technique, for example, generally may include selecting a targeted FOV 24 for a tomographic image (block 26) and deriving background projection data 28 for the area outside the targeted FOV (block 30). As will be appreciated, for CT reconstruction, the background projection data generally may represent attenuation of photon flux from the area outside the targeted FOV 24. Once the background projection data 28 is derived, the background projection data 28 may be used as an additional factor in the reconstruction of the targeted FOV (block 32), such as in a reconstruction utilizing the above-listed MLTR algorithm. Accordingly, equations (9) and (10) can be modified to implement the reconstruction technique described herein. Exemplary iterative update equations for the pre-correction technique and the corrections in the loop technique utilizing the background projection data in a MLTR algorithm are given by equations (11) and (12), respectively. It should be appreciated, however, that the present technique is applicable for implementation using any suitable iterative reconstruction update equation.

$$\mu_j^{k,m+1} = \mu_j^{k,m} + \frac{\sum_{i \in S_m} P_{i,j}(\hat{y}_i - y_i - S_i - t_i^{bkg})}{\sum_{i \in S_m} P_{i,j} \cdot \left[\sum_{j'} P_{i,j'}\right] \cdot \hat{y}_i} \quad (11)$$

$$\mu_j^{k,m+1} = \mu_j^{k,m} + \frac{\sum_{i \in S_m} P_{i,j} \cdot \frac{(\hat{y}_i - S_i - t_i^{bkg})}{\hat{y}_i} \cdot (\hat{y}_i - y_i)}{\sum_{i \in S_m} P_{i,j} \cdot \left[\sum_{j'} P_{i,j'}\right] \cdot (\hat{y}_i - S_i - t_i^{bkg}) \cdot \left(1 - \frac{y_i(S_i + t_i^{bkg})}{\hat{y}_i^2}\right)} \quad (12)$$

Wherein:

$\mu$ refers to an image estimate, and $\mu_j^{k,m}$ refers to the image estimate for pixel j at the $k^{th}$ iteration and the $m^{th}$ subset of LORs;

$P_{i,j}$ refers to the effective intersection length of the LOR i with pixel j;

$S_i$ refers to the scatter flux detected at the detector i;

$t_i^{bkg}$ refers to the projection data resulting from attenuation of photon flux from the area outside the targeted FOV (or the background projection data);

$\hat{y}_i$ refers to the mean photon flux detected at the detector $i^{th}$ in the presence of the object;

$y_i$ refers to the measured projection data detected by the $i^{th}$ LOR; and $S_m$ refers to the $m^{th}$ subset of LORs.

Figure 15:
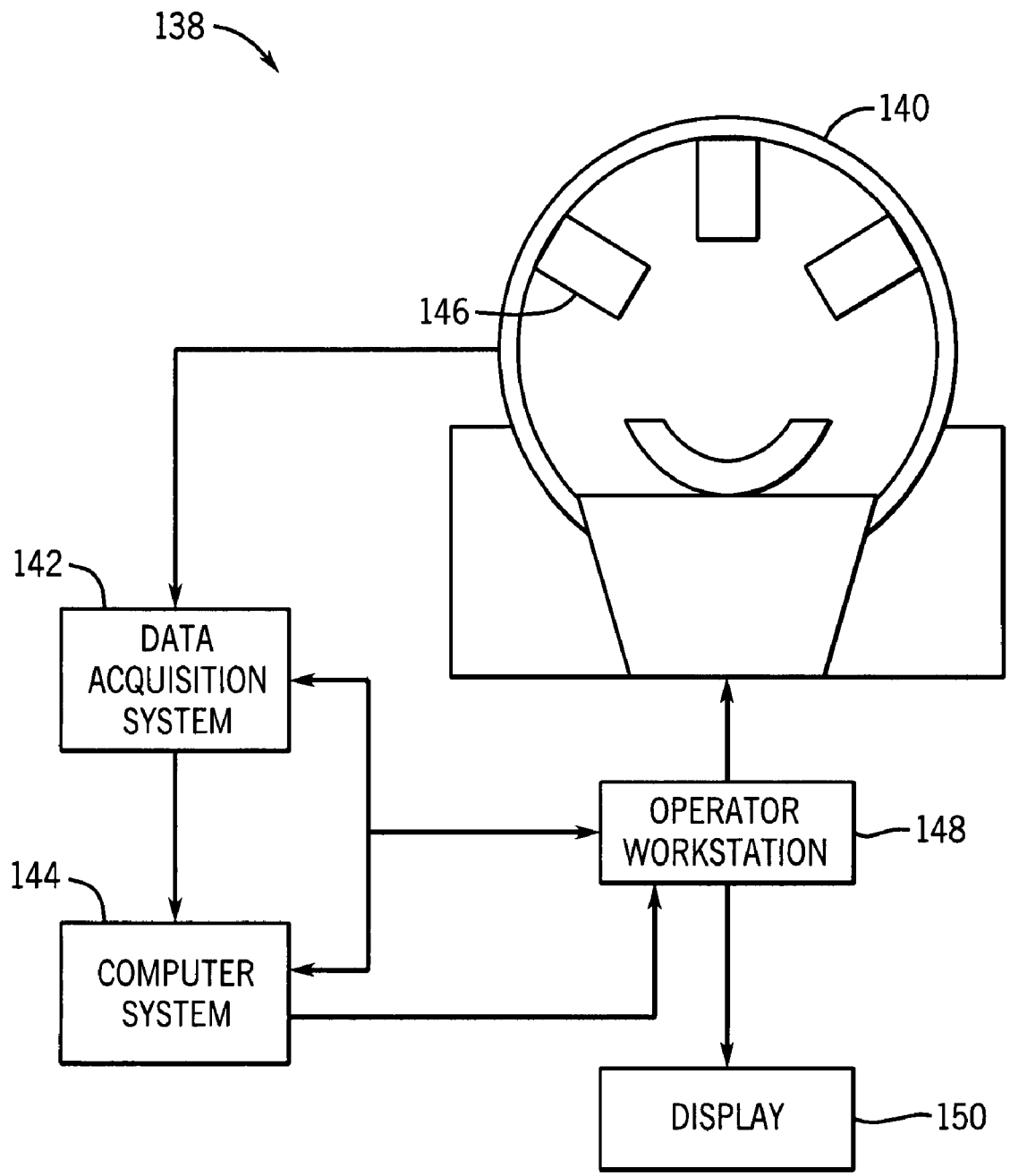
FIG. 15 is a diagrammatical illustration of an exemplary SPECT imaging system, in accordance with one embodiment of the present technique.

As previously noted, exemplary embodiments of the may be used for image reconstruction with imaging modalities that use line integral projection tomography reconstruction, such as SPECT imaging. FIG. 15 illustrates diagrammatically SPECT imaging system 138 designed both to acquire original image data, and to process the image data for display and analysis. The SPECT system 138 includes a detector assembly 140, a data acquisition system 142, and computer system 144. The detector assembly 140 typically includes a number of detector modules (generally represented by number 146) arranged around the FOV. The SPECT system 138 also includes an operator workstation 148 and a display 150. While in the illustrated embodiment, the data acquisition system 142, and the computer system 144 are shown as being outside the detector assembly 140 and the operator workstation 148, in certain other implementations, some or all of these components may be provided as part of the detector assembly 140 and/or the operator workstation 148.

As one of ordinary skill in the art will appreciate, the processes described herein may be provided as one or more routines executable by the computer system 16 or by other processor-based components of an imaging system, such as the PET system 10, the CT system 106, the SPECT system 138, and so forth. The routines may be stored or accessed on one or more computer-readable media, such as magnetic or optical media, which may be local to the computer system 16, or processor-based component, or may be remotely accessible via a network connection, such as the Internet or a local area network. Furthermore, access to or operation of the routines may be provided to an operator via the operator workstation 20 as part of the normal operation of an imaging system, such as the PET system 10, the CT system 106, the SPECT system 138, and so forth.

Exemplary embodiments of the present technique may use a variety of suitable iterative reconstruction algorithms for the SPECT reconstruction. As will be appreciated by those of ordinary skill in the art, the present technique may be implemented for SPECT reconstruction utilizing the OSEM algorithm. While the OSEM algorithm is shown below, exemplary embodiments of the present technique may be implemented using any suitable iterative reconstruction update equation. By way of example, exemplary iterative update equations for the pre-correction technique and the corrections in the loop technique utilizing the background projection data in an OSEM algorithm are given by equations (12) and (13), respectively:

$$\lambda_j^{k,m+1} = \frac{\lambda_j^{k,m}}{\sum_{i \in S_m} P_{i,j}} \sum_{i \in S_m} P_{i,j} \frac{y_i - t_i^{bkg} - r_i - s_i}{\sum_{j'} P_{i,j'} \lambda_{j'}^{k,m}} \quad (12)$$

$$\lambda_j^{k,m+1} = \frac{\lambda_j^{k,m}}{\sum_{i \in S_m} P_{i,j}} \sum_{i \in S_m} P_{i,j} \frac{y_i}{\sum_{j'} P_{i,j'} \lambda_{j'}^{k,m} + t_i^{bkg} + r_i + s_i} \quad (13)$$

Wherein:

$\lambda$ refers to an image estimate, and $\lambda_j^{k,m}$ refers to the image estimate for pixel j at the $k^{th}$ iteration and the $m^{th}$ subset of LORs;

y refers to the measured projection data for the scan FOV, and $y_i$ refers to the measured projection data detected by the $i^{th}$ LOR;

$r_i$ refers to the random coincidences detected by the $i^{th}$ LOR;

$s_i$ refers to the scatter coincidences detected by the $i^{th}$ LOR;

$P_{i,j}$ refers to the projection matrix that determines the probability that activity from pixel j is detected by $i^{th}$ LOR;

$t_i^{bkg}$ refers to the attenuated background projection data detected by the $i^{th}$ LOR; and $S_m$ refers to the $m^{th}$ subset of LORs.

It should be noted that the PET and SPECT reconstruction algorithms differ in their attenuation correction method. In PET reconstruction, attenuation correction may be performed on individual LORs because the attenuation process for all image pixels along an LOR should generally be the same. Therefore, the forward projection operator ($P_{i,j}$) and attenuation factor ($A_i$) can be separated. In SPECT reconstruction, all images pixels along an LOR do not have the same attenuation, e.g., the image pixels closest to the detector have the least attenuation. In other words, attenuation is dependent on the depth of the pixels from the detector. Therefore the forward projection operator and the attenuation factor cannot be separated. Accordingly, in SPECT reconstruction, the forward projection operator ($P_{i,j}$) may be computed in a manner so as to account for the attenuations.

EXAMPLE

To compare iterative reconstruction methods, a Monte Carlo simulation of a Zubal phantom was performed for the GE Discovery ST™ PET/CT scanner to generate prompts, randoms, and scatter projection datas. The full scan FOV was 32 centimeters. The targeted FOV was centered on the heart and was 10.6 centimeters. Three targeted reconstruction methods were employed, each using the OSEM algorithm.

The reconstruction methods differed in how activity outside the targeted FOV was handled. For the first reconstruction method, the signal from outside the targeted FOV was ignored by assigning all the signal from outside the targeted FOV to the periphery of the targeted FOV. This first reconstruction method may be referred to as a "naïve reconstruction." For the second reconstruction method, a brute-force reconstruction was employed, wherein the full scan FOV was reconstructed at high resolution from which the image for the targeted FOV was extracted. And for the third reconstruction method, the exemplary correction-in-the-loop OSEM algorithm of FIG. 11 was employed, wherein the background projection data was used as additional corrective term that was added to the forward projected image estimate 58.

The images of the targeted FOV for the first (naïve) reconstruction method and third (corrections-in-the-loop) reconstruction method were compared to the image generated using the second (brute-force) reconstruction method. From this qualitative analysis, the naïve reconstruction was observed to have visible artifacts on the periphery of the targeted FOV and subtle concentric ripples throughout the image. In contrast, the corrections-in-the-loop reconstruction had no visible artifacts and resulted in an image that was very similar to the reconstruction image from the brute-force method.

A quantitative comparison of these reconstruction techniques was also performed by measuring the mean and standard deviation of the activities on the heart wall, the left ventricle, and the adjoining lungs. The brute-force reconstruction results in the most quantitatively accurate data because it reconstructs every pixel in the FOV at the higher resolution. As illustrated by Table 2 below, the brute-force reconstruction and the corrections-in-the-loop reconstruction resulted in quantitatively equivalent images, while the naïve reconstruction resulted in biased measurements.

TABLE 2

|  | Naïve Reconstruction | Brute-Force Reconstruction | Corrections-in-the Loop Reconstruction |
|---|---|---|---|
| Ventricles | 0.1374 +/− .0834 | 0.1193 +/− 0.0656 | 0.1219 +/− 0.0531 |
| Heart Wall | 0.2834 +/− 0.1356 | 0.2595 +/− 0.1061 | 0.2592 +/− 0.0937 |
| Lungs | 0.0536 +/− 0.0496 | 0.0231 +/− 0.0165 | 0.0233 +/− 0.0136 |

In addition, the reconstruction times for the three reconstructions methods were also determined. The reconstructions were performed on a computer with a 1.6 gigahertz Pentium 4 process running MATLAB. The reconstruction times for each of the three reconstructions are shown below in Table 3.

TABLE 3

| Method | Reconstruction Time (sec) |
|---|---|
| Naïve Reconstruction | 39 |
| Brute-Force Reconstruction | 378 |
| Corrections-in-the-Loop Reconstruction | 44 |

As illustrated by the reconstruction times shown above in Table 3, the corrections-in-the-loop reconstruction resulted in an approximately 8.5 times faster reconstruction as compared to the brute-force reconstruction.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for performing image reconstruction, comprising:
    deriving background projection data for an area outside a targeted field of view and an area inside a scan field of view of a tomographic image;
    reconstructing the tomographic image of the targeted field of view, said reconstructing comprising:
        obtaining an image estimate of the scan field of view;
        forward projecting the image estimate of the scan field of view;
        comparing the targeted projection data with the forward projected image estimate to obtain a correction ratio;
        back projecting the correction ratio to obtain correction image data;
        applying the correction image data to the image estimate to obtain an updated image estimate, and
    wherein the background projection data is used in the reconstruction.

2. The method of claim 1, wherein the deriving the background projection data comprises masking pixels in a reconstructed image, wherein the masked pixels correspond to pixels inside the targeted field of view.

3. The method of claim 1, wherein the deriving the background projection data comprises:
    deriving measured projection data for the scan field of view of the tomographic image;
    reconstructing the measured projection data to obtain an image of the scan field of view;
    masking pixels in the reconstructed image of the scan field of view, wherein the masked pixels correspond to pixels inside the targeted field of view; and
    forward projecting the reconstructed image with the masked pixels to obtain the background projection data.

4. The method of claim 1, wherein the reconstructing the tomographic image of the targeted field of view comprises subtracting the background projection data from projection data for the scan field of view to obtain targeted projection data.

5. The method of claim 1, comprising applying attenuation to the background projection data so that the attenuated background projection data is subtracted from the projection data for the scan field of view.

6. The method of claim 1, wherein the reconstructing the tomographic image of the targeted field of view comprises:
    applying attenuation to the background projection data; and
    adding the attenuated background projection data to a forward projected image estimate of the targeted field of view to obtain a corrected forward projection.

7. The method of claim 6, wherein the reconstructing the tomographic image of the targeted field of view comprises:
    comparing the corrected forward projection to a measured projection data for the scan field of view to obtain a correction ratio;
    back projecting the correction ratio to obtain correction image data; and
    applying the correction image data to the image estimate to obtain an updated image estimate.

8. The method of claim 1, wherein the reconstructing the tomographic image of the targeted field of view comprises utilizing an Ordered Subsets Expectation Maximization algorithm or a Maximum Likelihood Transmission algorithm.

9. The method of claim 1, wherein the image reconstruction is applied to four dimensions, wherein the fourth dimension is time dependent gating.

10. The method of claim 9, wherein the background projection data is not time dependent while projection data is acquired based on time dependent gating, and wherein the reconstructing the tomographic image of the targeted field of view comprises scaling the background projection data by the relative acquisition time of each gate to obtain gated background projection data for each corresponding gate.

11. The method of claim 1, wherein the targeted field of view is selected by a user, is automatically selected, or is semi-automatically selected.

12. The method of claim 1, wherein the targeted field of view comprises a selected field of view plus a buffer zone.

13. The method of claim 1, wherein the background projection data is a projection data resulting from attenuation of photon flux from the area outside the targeted field of view.

14. The method of claim 1, wherein the targeted field of view is less than or equal to the scan field of view.

15. A method for selecting a reconstruction methodology, comprising:
    determining a number of pixels in a reconstructed image for a first reconstruction methodology;
    determining a number of pixels in a reconstructed image for a second reconstruction methodology;
    comparing the number of pixels for the first reconstruction methodology and the number of pixels for the second reconstruction methodology; and
    selecting the reconstruction methodology for image reconstruction based on the comparison of the number of pixels.

16. The method of claim 15, wherein the number of pixels in the reconstructed image for the first reconstruction methodology is represented by the following equation:

$$\left(\frac{N_T SFOV}{TFOV}\right)^2$$

wherein $N_T$ is the size of a pixel grid for a targeted reconstruction, SFOV is a diameter of a scan field of view, and TFOV is a diameter of the targeted field of view.

17. The method of claim 15, wherein the number of pixels in the reconstructed image for the second reconstruction methodology is represented by the following equation:

$$N_F^2 \left[N_T * \left(1 + \frac{2\sqrt{2}\, SFOV}{N_F TFOV}\right)\right]^2$$

wherein $N_F$ is the number of pixels for full scan field of view, $N_T$ is the size of the pixel grid for a targeted reconstruction, SFOV is the diameter of a scan field of view, and TFOV is the diameter of a targeted field of view.

18. An imaging system comprising:
    image reconstruction and processing circuitry configured to derive background projection data for an area outside a targeted field of view of a tomographic image and an area inside a scan field of view, to obtain an image estimate of the scan field of view, to forward project the image estimate of the scan field of view, to compare the targeted projection data with the forward projected image estimate to obtain a correction ratio, to back project the correction ratio to obtain correction image data, and to apply the correction image data to the image estimate to obtain an updated image estimate and to reconstruct the tomographic image of the targeted field of view, wherein the background projection data is used in the reconstruction.

19. The method of claim 18, wherein the image reconstruction and processing circuitry is configured to mask pixels in a reconstructed image to derive the background projection data, wherein the masked pixels correspond to pixels inside the targeted field of view.

20. The imaging system of claim 18, wherein the image reconstruction and processing circuitry is configured to derive measured projection data for a scan field of view of the tomographic image, to reconstruct the measured projection data to obtain an image of the scan field of view, to mask pixels in the reconstructed image of the scan field of view, wherein the masked pixels correspond to pixels inside the targeted field of view, and to forward project the reconstructed image with the masked pixels to obtain the background projection data.

21. The imaging system of claim 18, wherein the image reconstruction and processing circuitry is configured to subtract the background projection data from a projection data for the scan field of view to obtain targeted projection data.

22. The imaging system of claim 18, wherein the image reconstruction and processing circuitry is configured to apply attenuation to the background projection data, and add the attenuated background projection data to a forward projected image estimate of the targeted field of view to obtain a corrected forward projection.

23. The imaging system of claim 22, wherein the image reconstruction and processing circuitry is configured to compare the corrected forward projection to measured projection data for the scan field of view to obtain a correction ratio, to back project the correction ratio to obtain correction image data, and to apply the correction image data to the image estimate to obtain an updated image estimate.

24. The imaging system of claim 18, wherein the reconstruction is applied to four dimensions, wherein the fourth dimension is time dependent gating.

25. The imaging system of claim 18, wherein the imaging system is a PET system, a CT system, a SPECT system, or any other imaging system that uses line integral projection tomography reconstruction, or a combination thereof.

26. An imaging system comprising:
image reconstruction and processing circuitry configured to determine a number of pixels in a reconstructed image for a first reconstruction methodology, to determine a number of pixels in a reconstructed image for a second reconstruction methodology, to compare the number of pixels for the first reconstruction methodology and the number of pixels for the second reconstruction methodology, and to select the reconstruction methodology for image reconstruction based on the comparison of the number of pixels.

27. The imaging system of claim 26, wherein the imaging system is a PET system, a CT system, a SPECT system, or any other imaging system that uses line integral projection tomography reconstruction, or a combination thereof.

28. A computer program, stored on a computer readable medium, for performing image reconstruction, the program constructed and arranged to derive background projection data for an area outside a targeted field of view of a tomographic image and an area inside a scan field of view, and to reconstruct the tomographic image of the targeted field of view by the steps comprising:
obtaining an image estimate of the scan field of view;
forward projecting the image estimate of the scan field of view;
comparing the targeted projection data with the forward projected image estimate to obtain a correction ratio;
back projecting the correction ratio to obtain correction image data;
applying the correction image data to the image estimate to obtain an updated image estimate, and
wherein the background projection data is used in the reconstruction.

29. A computer program, stored on a computer readable medium, for performing image reconstruction, the program constructed and arranged to determine a number of pixels in a reconstructed image for a first reconstruction methodology, to determine a number of pixels in a reconstructed image for a second reconstruction methodology, to compare the number of pixels for the first reconstruction methodology and the number of pixels for the second reconstruction methodology, and to select the reconstruction methodology for image reconstruction based on the comparison of the number of pixels.

* * * * *

UNITED STATES PATENT AND TRADEMARK OFFICE
CERTIFICATE OF CORRECTION

| | | |
|---|---|---|
| PATENT NO. | : 7,680,240 B2 | Page 1 of 1 |
| APPLICATION NO. | : 11/731612 | |
| DATED | : March 16, 2010 | |
| INVENTOR(S) | : Manjeshwar et al. | |

It is certified that error appears in the above-identified patent and that said Letters Patent is hereby corrected as shown below:

In Column 16, Lines 2-7, in Equation (11), delete " $$\mu_j^{k,m+1} = \mu_j^{k,m} + \frac{\sum_{i \in S_m} P_{i,j}(\hat{y}_i - y_i - S_i - t_i^{bkg})}{\sum_{i \in S_m} P_{i,j} \cdot \left[\sum_{j'} P_{i,j'}\right] \cdot \hat{y}_i}$$ " and insert -- $$\mu_j^{k,m+1} = \mu_j^{k,m} + \frac{\sum_{i \in S_m} P_{i,j}(\hat{y}_i - y_i - S_i - t_i^{bkg})}{\sum_{i \in S_m} P_{i,j} \cdot \left[\sum_{j'} P_{i,j'}\right] \cdot \hat{y}_i}$$ --, therefor.

In Column 17, Line 56, delete "($P_{ij}$)" and insert -- ($P_{i,j}$) --, therefor.

In Column 21, Line 10, in Claim 19, delete "The method" and insert -- The imaging system --, therefor.

Signed and Sealed this
Fourteenth Day of June, 2011

David J. Kappos
*Director of the United States Patent and Trademark Office*